US009220736B2

(12) United States Patent
Farmer et al.

(10) Patent No.: US 9,220,736 B2
(45) Date of Patent: *Dec. 29, 2015

(54) METHODS FOR THE DIETARY MANAGEMENT OF IRRITABLE BOWEL SYNDROME AND CARBOHYDRATE MALABSORPTION

(75) Inventors: Sean Farmer, Miami Beach, FL (US); Andrew R. Lefkowitz, Beachwood, OH (US)

(73) Assignee: Ganeden Biotech, Inc., Mayfield Heights, OH (US)

( * ) Notice: Subject to any disclaimer, the term of this patent is extended or adjusted under 35 U.S.C. 154(b) by 1216 days.

This patent is subject to a terminal disclaimer.

(21) Appl. No.: 11/985,617

(22) Filed: Nov. 15, 2007

(65) Prior Publication Data
US 2008/0112942 A1    May 15, 2008

Related U.S. Application Data

(60) Division of application No. 10/915,030, filed on Aug. 9, 2004, now Pat. No. 7,767,203, which is a continuation-in-part of application No. 09/369,016, filed on Aug. 5, 1999, now abandoned.

(60) Provisional application No. 60/095,786, filed on Aug. 7, 1998, provisional application No. 60/528,074, filed on Dec. 5, 2003.

(51) Int. Cl.
| *A61K 45/06* | (2006.01) |
| *A61K 35/744* | (2015.01) |
| *A23L 1/30* | (2006.01) |
| *A61K 35/742* | (2015.01) |
| *A61K 38/46* | (2006.01) |
| *A61K 38/47* | (2006.01) |

(52) U.S. Cl.
CPC ............... *A61K 35/744* (2013.01); *A23L 1/30* (2013.01); *A23L 1/3014* (2013.01); *A61K 35/742* (2013.01); *A61K 38/465* (2013.01); *A61K 38/47* (2013.01); *A61K 45/06* (2013.01)

(58) Field of Classification Search
None
See application file for complete search history.

(56) References Cited

U.S. PATENT DOCUMENTS

| 3,629,073 A | 12/1971 | Cayle .............................. 195/62 |
| 3,718,739 A | 2/1973 | Cayle .............................. 424/94 |
| 3,919,049 A | 11/1975 | Kiuchi et al. ................... 195/66 |
| 4,110,477 A | 8/1978 | Naruse et al. ................... 426/46 |
| 4,179,335 A | 12/1979 | Long et al. ...................... 435/99 |
| 4,210,672 A | 7/1980 | Hata .............................. 426/43 |
| 4,323,651 A | 4/1982 | Long et al. ..................... 435/207 |
| 4,751,085 A | 6/1988 | Gaull ............................ 424/145 |
| 4,806,368 A | 2/1989 | Reddy ........................... 426/61 |
| 4,980,180 A | 12/1990 | Cully et al. ..................... 426/47 |
| 5,079,164 A | 1/1992 | Kirkovits et al. .......... 435/252.5 |
| 5,102,800 A | 4/1992 | Hirikoshi ...................... 435/193 |
| 5,176,911 A | 1/1993 | Tosi et al. ....................... 424/93 |
| 5,200,336 A | 4/1993 | Kong et al. .................... 435/199 |
| 5,439,678 A | 8/1995 | Dobrogosz et al. ......... 424/93.45 |
| 5,449,523 A | 9/1995 | Hansen et al. .................. 426/42 |
| 5,520,936 A | 5/1996 | Delespaul et al. .............. 426/61 |
| 5,531,989 A | 7/1996 | Paul ............................ 424/93.4 |
| 5,538,743 A | 7/1996 | Heinemann et al. ............ 426/42 |
| 5,785,990 A | 7/1998 | Langrehr ....................... 424/442 |
| 5,968,569 A | 10/1999 | Cavadini et al. ................ 426/61 |
| 6,004,551 A | 12/1999 | Reid et al. ................... 424/93.45 |
| 6,410,018 B1 | 6/2002 | Eisenhardt et al. .......... 424/94.6 |
| 6,429,209 B2 | 8/2002 | Mangel et al. ................ 514/292 |
| 6,849,256 B1 | 2/2005 | Farmer ...................... 424/93.46 |
| 2005/0100535 A1 | 5/2005 | Farmer et al. .............. 424/93.46 |
| 2008/0038240 A1 | 2/2008 | Farmer et al. .............. 424/93.46 |

FOREIGN PATENT DOCUMENTS

| WO | WO 93/14187 | 7/1993 |
| WO | WO 94/11492 | 5/1994 |
| WO | WO 98/54982 | 12/1998 |
| WO | WO-00/07606 | 2/2000 |
| WO | WO-01/34168 A1 | 5/2001 |

OTHER PUBLICATIONS

Mohan et al. Indian J Med Res [B] 92, Dec. 1990, pp. 431-432.*
Farmer et al., The only GRAS-listed Bacillus Probiotic. Empower. Dec. 1997, pp. 5-7, 42-43.*
Farmer et al., Bacillus coagulans. Cholesterol: Fact and Theory, Empower. Jan. 1998, pp. 8, 38-41.*
Fink et al., Current Treatment Options in Gastroenterology 2001, 4:333-337.*
http://web.archive.org/web/20000604035747/http://www.microbax.com/product_.htm, accessed Aug. 22, 2008.
*ATCC Catalogue of Bacteria and Bacteriophages*, 19th Edition, p. 45 (1996).
Baker et al., "Growth Requirements of 94 Strains of Thermophilic Bacilli", *Canadian J. Microbiol.*, 6:557-563 (1960).
*Bergey's Manual of Systematic Bacteriology*, vol. 2, Sneath et al., eds., Williams & Wilkens, Baltimore, MD, p. 1117 (1986).
Choi et al., "Fructose Intolerance: An Under-Recognized Problem", *Am. J. Gastroenterol.*, 98(6) 1348-1353 (2003).
Evans et al., "Fructose-Sorbitol Malabsorption and Symptom Provocation in Irritable Bowel Syndrome: Relationship to Enteric Hypersensitivity and Dysmotility", *Scandinavian J. Gastroenterol.*, 33(11):1158-1163 (1998).
Farmer et al., "Bacillus coagulans—Cholesterol: Fact & Theory", *Empower*, 8:38-41 (1998).
Farmer et al., "Bacillus coagulans—the only GRAS-listed bacillus probiotic", *Empower*, pp. 5-7 and 42-43 (1997).

(Continued)

*Primary Examiner* — Irene Marx
(74) *Attorney, Agent, or Firm* — Ingrid A. Beattie

(57) ABSTRACT

The invention relates generally to digestive disorders, and in particular to methods for treating irritable bowel syndrome by increasing carbohydrate absorption by administering a composition containing a *Bacillus coagulans* bacterium.

21 Claims, No Drawings

(56) References Cited

OTHER PUBLICATIONS

Food Chemicals Codex, Third Ed., Nat'l. Acad. Press, Washington, DC, pp. 491-492 (1981).
Friend et al., "Nutritional and therapeutic aspects of lactobacilli", *J. Applied Nutrition*, 36(2):125-153 (1984).
Fuller, R., "A Review: Probiotics in man and animals", *J. Appl. Bacteriol.*, 66:365-378 (1989).
Fuller, R., "History and Development of Probiotics", In Probiotics: the Scientific Basis, London: Chapman & Hall, Chapter One, pp. 1-8 (1992).
Gibson et al., "Selective stimulation of bifidobacteria in the human colon by oligofructose and inulin", *Gastroenterol.*, 108(4):975-982 (1995).
Goldstein et al., "Carbohydrate Malabsorption and the Effect of Dietary Restriction on Symptoms of Irritable Bowel Syndrome and Functional Bowel Complaints", *IMAJ*, 2:583-587 (2000).
Hata et al., "Meningitis caused by bifidobacterium in an infant", *Pediatr. Infect. Dis.*, 7(9):669-671 (1988).
Hill et al., "Vaginitis: current microbiologic and clinical concepts", *Can. Med. Assoc. J.*, 134(4):321-331 (1986).
Hugenholtz, J., "Citrate metabolism in lactic acid bacteria", *FEMS Microbiol Rev.*, 12:165-178 (1993).
Kreuzer, M., "Probiotic-antibiotic interactions in performance, intestinal fermentation and manure properties of piglets using a Bacillus (B. licheniformis/B. subtilis) preparation and Carbadox", *Agribiol. Res.*, 47(1):13-23 (1994).
Lieberman et al., *Pharmaceutical Dosage Forms—Tablets*, vol. 3, Marcel Dekker, Inc., New York, NY, pp. 114-116 (1990).
Marsh, P.D., "Antimicrobial strategies in the prevention of dental caries", *Caries Res.*, 27(Suppl. 1):72-76 (1993).
Mitchell, P., "Rearming in the fight against bacteria", *Lancet*, 352:462 (1998).
Muastapha et al., "Improvement of lactose digestion by humans following ingestion of unfermented acidophilus milk: influence of bile sensitivity, lacatose transport, and acid tolerance of lactobacillus acidophilus", *J. Dairy Sci.*, 80:1537-1545 (1997).
Nairn, J.G., "Solutions, Emulsions, Suspensions and Extracts", *Remington's 18th Ed.*, Chapter 83, Mack Publishing Co., Easton, PA, pp. 1519-1544 (1990).
Nakamura et al., "Taxonomic Study of *Bacillus coagulans* Hammer 1915 with a Proposal for *Bacillus smithii* sp. nov.", *Inter'l J. Systematic Bacteriol.*, 38(1): 63-73 (1988).
Oyarzabal et al., "In Vitro fructooligasaccharide utilization and inhibition of *Salmonella* spp. by selected bacteria", *Poultry Sci.*, 74(9):1418-1425 (1995).
Patent Abstracts of Japan for JP 01083025 A (1989).
Patent Abstracts of Japan for JP 06343419 A (1994).
Reid et al., "Is there a role for lactobacilli in prevention of urogenital and intestinal infections?" *Clin. Microbiol. Rev.*, 3(4):335-344 (1990).
Rudnic, E. & Schwartz, J.B., "Oral Solid Dosage Forms", *Remington's 18th Ed.*, Chapter 89, Easton, PA, pp. 1633-1665 (1990).
Saavedra et al., "Feeding of Bifidobacterium bifidum and *Streptococcus thermophilus* in infants in hospital for prevention of diarrhea and shedding of rotavirus", *Lancet*, 344:1046-1049 (1994).
Salminen et al., "Functional food science and gastrointestinal physiology and function", *Br. J. Nutrition*, 80(Suppl. 1):S147-S171 (1998).
Shannon et al., "Multiple-antibiotic-resistant *Salmonella*", *Lancet*, 352:490(1998).
Somogyi, M., "Modifications of Two Methods for the Assay of Amylase", *Clin. Chem.*, 6(1):23-35 (1960).
Sussman et al., "Clinical manifestations and therapy of lactobacillus endocarditis: report of a case and review of the literature", *Rev Infect. Dis.*, 8(5):771-776 (1986).
Thomason et al., "Bacterial vaginosis: current review with indcations for asymptomatic therapy", *Am. J. Obstet. Gynecol.*, 165(4):1210-1217 (1991).
Thompson et al., "Functional bowel disorders and functional abdominal pain", *Gut*, 45(Suppl. II):II43-II47 (1999).
Thompson et al., "Irritable Bowel Syndrome: Guidelines for the Diagnosis", *Gastroenterology Inter'l.*, 2(2):92-95 (1989).
Thompson, W.G., "Irritable bowel syndrome: pathogenesis and management", *Lancet*, 341:1569-1572 (1993).
Tietz, N.W., & Fiereck, E.A., "A Specific Method for Serum Lipase Determination", *Clin. Chim. Acta*, 13(3):352-358 (1966).
*Townsend Lett. for Doctors and patients*, pp. 108-110 (1994).
Winberg et al., "Pathogenesis of urnary tract infection—experimental studies of vaginal resistance to colonization", *Pediatr. Nephrol.*, 7:509-514 (1993).
Ziemer et al., "An overview of probiotics, prebiotics and symbiotic in the functional food concept: perspectives and future strategies", *Int. Dairy J.*, 8:473-479 (1998).
Ara et al. "Effect of Spore-Bearing Lactic Acid-Forming Bacteria (*Bacillus coagulans* SANK 70258) Administration on the Intestinal Environment, Defecation Frequency, Fecal Characteristics and Dermal Characteristics in Humans and Rats." *Microbial Ecol. Health Dis.* 14.1(2002):4-13.
Chandra et al. "Effect of *Lactobacillus* on the Incidence and Severity of Acute Rotavirus Diarrhoea in Infants." *Nut. Res.* 22.1-2(2002):65-69.
Cui et al. "Efficacy of *Bacillus coagulans* Tablets in the Treatment of Acute and Chronic Diarrhea." *Int. J. Immunother.* 20.1(2004):17-22.
La Rosa et al. "Prevention of Antibiotic-Associated Diarrhea With *Lactobacillus sporogens* and Fructo-Oligosaccharides in Children." *Minerva Pediatrica.* 55.5(2003):447-452. (English Abstract Only).

\* cited by examiner

METHODS FOR THE DIETARY MANAGEMENT OF IRRITABLE BOWEL SYNDROME AND CARBOHYDRATE MALABSORPTION

RELATED APPLICATIONS

This application is a divisional of U.S. Ser. No. 10/915,030, filed Aug. 9, 2004, Now U.S. Pat. No. 7,767,203 which is a continuation-in-part of U.S. Ser. No. 09/369,016 filed Aug. 5, 1999, now abandoned which claims the benefit of U.S. Ser. No. 60/095,786, filed Aug. 7, 1998. This application also claims priority to U.S. Ser. No. 60/528,074, filed Dec. 5, 2003. Each application from which the present application claims priority is incorporated herein by reference in its entirety.

TECHNICAL FIELD OF THE INVENTION

The present invention relates to the utilization of probiotic lactic acid-producing bacteria in a nutritional composition. More specifically, the present invention relates to the use of *Bacillus coagulans* for increasing the absorption of carbohydrates within the gastrointestinal tract of a mammal.

BACKGROUND OF THE INVENTION

The human digestive system uses a series of enzymes to break down complex foods into simple molecules (e.g., sugars, peptides and lipids) that can be absorbed by the body. The inability or diminished capacity of the body's production of one or more enzymes that are crucial for proper digestion can lead to gastrointestinal symptoms that have been characterized by the medical community as irritable bowel syndrome (IBS). A patient with IBS typically presents clinically with one of three variants: i) chronic abdominal pain and constipation (also known as spastic colitis); ii) chronic intermittent diarrhea, often without pain; or iii) both features, in an alternating cycle of constipation and diarrhea.

SUMMARY OF THE INVENTION

The invention is based, in part, on the discovery of the therapeutic effects of *Bacillus coagulans*, a spore-forming lactic acid bacterium, in the prevention and treatment of IBS and carbohydrate malabsorption. Carbohydrate malabsorption includes the inability of a mammal to fully digest the naturally occurring sugars (e.g., lactose, fructose, and glucose) in foods and beverages.

In one aspect, the invention provides a method of reducing one or more symptoms of irritable bowel syndrome, by identifying a patient suffering from or at risk of developing irritable bowel syndrome, and administering to the patient a composition that includes *Bacillus coagulans* bacteria. Bacterial species include *Bacillus coagulans*, e.g., *Bacillus coagulans* hammer, preferably *Bacillus coagulans* hammer strain Accession No. ATCC 31284, or strains derived from *Bacillus coagulans* hammer strain Accession No. ATCC 31284, such as, GBI-20 (ATCC Designation Number PTA-6085); GBI-30 (ATCC Designation Number PTA-6086); and GBI-40 (ATCC Designation Number PTA-6087). (See, copending U.S. patent application Ser. No. 09/708,870, the contents of which are incorporated by reference in their entirety). Symptoms of IBS include diarrhea, constipation, alternating diarrhea and constipation, gas, bloating, urgency, and abdominal pain (intestinal discomfort). The composition also includes a supplementary enzyme (e.g., a lactase, a fructase, a lipase, or a protease), an anti-diarrheal agent (e.g., loperamide, attapulgite, Croton Lechleri Extract, or calcium polycarbophil), an anti-gas agent (e.g., α-galactosidase enzyme, simethicone, calcium carbonate, aluminum hydroxide or magnesium hydroxide), or a laxative (e.g., a senoside such as senosides A, B, C or D, docusate sodium, magnesium hydroxide, or a dietary fiber). A supplemental lactase includes an enzyme that catalyzes the hydrolysis of lactose in the gastrointestinal tract of a mammal, in a concentration that exceeds the amount of lactase that is present in the small or large intestine of a mammal prior to *Bacillus coagulans* colonization. The composition contains an isolated lactose, i.e., an enzyme that has been purified from a cell which produces the enzyme. A supplemental fructase includes an enzyme that catalyzes the hydrolysis of fructose in the gastrointestinal tract of a mammal, in a concentration that exceeds the amount of fructase that is present in the small or large intestines of a mammal prior to *Bacillus coagulans* colonization. The gastrointestinal tract is the system of organs in a mammal including the mouth (buccal cavity), pharynx, esophagus and cardia, stomach(s), and intestines.

Colonization of *Bacillus coagulans* bacteria generally occurs between 24-48 hours following delivery. Continued colonization is improved by the repeated administration of *Bacillus coagulans*, such as daily administration. Generally, the supplementary fructase is provided at a dose of from about 1000 IU to about 12,000 IU, and the supplementary lactase is provided at a dose of from about 1000 IU to about 12,000 IU. In some treatment regimens, the target patient pool is female, such as a female that is post-menstrual or post-menopausal. Alternatively, the patient is male.

A therapeutic does includes *Bacillus coagulans* bacteria at a concentration of from about $1 \times 10^4$ to about $1 \times 10^{12}$ viable bacteria, specifically about $1 \times 10^6$ to about $1 \times 10^{11}$, more specifically about $1 \times 10^8$ to about $1 \times 10^{10}$, and most specifically about $8 \times 10^8$. The *Bacillus coagulans* bacteria are in the form of spores, vegetative cells, or a combination thereof.

The invention also provides a method of reducing one or more symptoms of irritable bowel syndrome, by identifying a patient suffering from or at risk of developing irritable bowel syndrome, and administering to the patient a composition including an effective IBS inhibiting amount of *Bacillus coagulans* bacteria prior to or concomitant with the onset of one or more IBS symptoms. Symptoms of IBS include diarrhea, constipation, alternating diarrhea and constipation, bloating, urgency, and abdominal pain.

In another aspect, the invention, the invention provides a method of reducing a symptom of irritable bowel syndrome, by identifying a patient suffering from or at risk of developing irritable bowel syndrome, and administering to the patient a composition that includes a supplementary enzyme, preferably a fructase and a lactase.

The invention also provides a method of diagnosing irritable bowel syndrome in a patient, including the steps of identifying a patient having a symptom of irritable bowel syndrome, providing a patient-derived biological sample from the identified patient, determining an amount of a product of a gastrointestinal enzyme in the patient-derived sample, and comparing the amount in the patient-derived sample with a reference amount of a product of a gastrointestinal enzyme, whereby an alteration in the test amount relative to the reference amount indicates that the patient has irritable bowel syndrome.

A gastrointestinal enzyme includes any enzyme that is active in the gastrointestinal tract, particularly the stomach and the small and large intestines. A biological sample includes any solid, liquid, or gaseous material obtained from a mammal, such as a human patient. The symptoms of IBS include diarrhea, constipation, or alternating diarrhea and constipation. The gastrointestinal enzyme includes a lactase, a fructase, a lipase and a protease. In embodiments of the invention, the patient identified as having a symptom of irritable bowel syndrome has one or more symptoms classified under the Rome Criteria. The amount of the product of a gastrointestinal enzyme in the patient-derived sample is modulated following administration of the compositions of the invention. For example, hydrogen measured using the hydrogen breath test declines following administration of a *Bacillus coagulans*-containing composition.

In another aspect, the invention provides a method of improving stool consistency in a patient afflicted with non-constipated IBS, by administering an effective amount of a *Bacillus coagulans* bacteria provided at a concentration of from about $1\times10^8$ to about $1\times10^{10}$ viable bacteria, where the patient's stool consistency is improved following the administration. For example, abnormal patient stool is characterized as lumpy/hard or loose/watery and an improvement includes less constipated or diarrhea stool.

In a further aspect, the invention relates to a method of decreasing urgency in a subject afflicted with IBS, by administering an effective amount of a *Bacillus coagulans* bacteria provided at a concentration of from about $1\times10^8$ to about $1\times10^{10}$ viable bacteria wherein urgency is decreased following the administration. Incontinence of stool is an inability to control or delay bowel movements until an appropriate time, e.g., until one can get to a toilet. Urgency is a sudden urge to have a bowel movement that is so strong that if a toilet is not immediately available, incontinence will occur.

The invention also provides a composition that includes a *Bacillus coagulans* bacteria, a supplementary lactase (e.g., β-galactosidase), and a supplementary fructase. Generally, the supplementary lactase is provided in a concentration from about 1000 IU to about 12,000 IU (e.g., about 3000 IU), and the supplementary fructase is provided in a concentration from about 1000 IU to about 12,000 IU (e.g., about 3000 IU). The composition also includes an anti-diarrheal agent, an anti-gas agent, a laxative, a vitamin, a mineral, an isolated amino acid, a source of dietary fiber, or an antibiotic. The composition may also include a pharmaceutically-acceptable carrier containing, e.g., silicone. The composition is in the form of a capsule, tablet (including a chewable tablet), powder, liquid or in a formulation with a food product. Food products include dairy products including ice cream, nutritional bars (energy or candy bars), sugar substitutes, non-dairy creamers, tea bags, and similar products. Sources of dietary fiber include psyllium husk, soy fiber, citrus fiber, beet fiber, pumpkin seed meal, ground flax, black walnut hull, rice fiber, hydrocollodial polysaccharides, pecan husks, and peanut husks.

The invention provides a composition containing a *Bacillus coagulans* bacteria and a supplemental enzyme provided in a formulation with a food product. For example, the food product is a dairy product (a product containing a component obtained from the milk of a cow, sheep, goat, or similar mammal).

The invention further provides a composition that includes from about $1\times10^8$ to about $1\times10^{10}$ *Bacillus coagulans* bacteria, a supplemental lactase in a concentration of about 3000 IU, a supplemental fructase in a concentration of about 3000 IU, and manganese stearate.

The invention also provides a composition that includes an isolated lactase provided in a concentration from about 1000 IU to about 12,000 IU per dose and an isolated fructase provided in a concentration from about 1000 IU to about 12,000 IU per dose. The composition also includes an anti-diarrheal agent, an anti-gas agent, a laxative, a vitamin, a mineral, an isolated amino acid, a source of dietary fiber, an antibiotic, or a combination thereof.

The invention also provides a method for increasing carbohydrate absorption in a mammal, by administering to a mammal a composition that includes a *Bacillus coagulans* bacteria, a supplementary lactase (e.g., provided in a concentration from about 1000 IU to about 12,000 IU), and a supplementary fructase (e.g., provided in a concentration from about 1000 IU to about 12,000 IU), where carbohydrate absorption is increased following the administration. The mammal is diagnosed as suffering from or being at risk of developing a disorder associated with carbohydrate malabsorption. Disorders associated with carbohydrate malabsorption include lactose intolerance, fructose intolerance, glucose-galactose intolerance, sorbitol intolerance, irritable bowel syndrome, short bowel syndrome, stagnant loop syndrome, celiac disease, chronic malnutrition, chronic persistent diarrhea, immunoproliferative small intestinal disease, intractable diarrhea of infancy, postenteritis syndrome, tropical sprue, Whipple's disease, Wolman disease, Crohn's disease and ulcerative colitis. The composition optionally includes an anti-diarrheal agent, an anti-gas agent, a laxative, a vitamin, a mineral, an isolated amino acid, a source of dietary fiber, or an antibiotic.

The invention further provides a method for increasing lactose digestion, including the steps of identifying a patient suffering from or at risk of developing lactose intolerance, and administering to the patient a composition that includes *Bacillus coagulans* bacteria and a supplemental lactase (e.g., provided in a concentration from about 1000 IU to about 12,000 IU), whereby lactose digestion is increased following the administration.

The invention also provides a composition including a *Bacillus coagulans* bacteria and a supplementary fructase, e.g., a fructase provided in a concentration from about 1000 IU to about 12,000 IU. The composition also includes an isolated amino acid. The composition is provided in the form of a capsule, tablet (including chewable tablet), powder, liquid or in a formulation with a food product. The *Bacillus coagulans* bacteria are derived from *Bacillus coagulans* Hammer strain Accession No. ATCC 31284.

In another aspect, the invention provides a medical food for the management of irritable bowel syndrome, that includes *Bacillus coagulans* bacteria and an isolated amino acid (e.g., L-lysine), wherein said medical food is formulated to provide at least about $1\times10^6$ (e.g., $1\times10^7$, $1\times10^8$ or $8\times10^8$ or more) viable *Bacillus coagulans* bacteria in the gastrointestinal tract of a mammal per day based on a serving size of about 0.5 gram to about 25 grams of the medical food taken up to twice a day. In embodiments of the invention, the medical food is provided at a dosage such that colonization of about $1\times10^5$ (e.g., $1\times10^6$ or $1\times10^7$) viable *Bacillus coagulans* bacteria per gram of fecal material in a mammal following consumption of the medical food. In embodiments of the invention, the medical food includes a supplemental enzyme such as a lactase, a fructase, a lipase or a protease. In other embodiments, the medical food includes an anti-diarrheal agent, an anti-gas agent, a laxative, a vitamin, a mineral, an appropriate amino acid(s), a source of dietary fiber, and/or an antibiotic.

In a further aspect, the invention provides a method of dietary management of a subject's carbohydrate absorption, including the steps of identifying a patient having a symptom of carbohydrate malabsorption, and providing a composition comprising *Bacillus coagulans* bacteria to the identified patient, wherein the bacteria colonize the subject's gastrointestinal tract, whereby carbohydrate absorption by the subject is modulated, such that the subject's carbohydrate absorption and is managed. The dietary management of the subject's carbohydrate absorption results in a reduction or elimination of one or more of the symptoms of carbohydrate malabsorption.

In another aspect, the invention provides a method of dietary management of a subject's carbohydrate absorption, including the steps of identifying a patient having a symptom of carbohydrate malabsorption, providing a patient-derived biological sample from the identified patient, determining an amount of a product of a gastrointestinal enzyme in the patient-derived sample, comparing the amount in the patient-derived sample with a reference amount of a product of a gastrointestinal enzyme, and providing a composition comprising *Bacillus coagulans* bacteria, whereby the subject's carbohydrate absorption is managed. The amount of a product of a gastrointestinal enzyme in the patient-derived sample is determined using hydrogen and/or methane breath testing. The amount of the product in the patient-derived sample declines following administration of the *Bacillus coagulans*-containing composition. The patient's carbohydrate absorption is managed such that one or more symptoms of carbohydrate malabsorption are decreased or eliminated.

The invention further provides a method for increasing carbohydrate absorption in a patient diagnosed as suffering from or being at risk of developing celiac disease, by administering to the subject a composition comprising *Bacillus coagulans* bacteria, wherein carbohydrate absorption in the patient is increased following the administration.

In another aspect, the invention provides a method of reducing a symptom of IBS, wherein the symptom includes alternating diarrhea and constipation, by identifying a patient suffering from or at risk of developing irritable bowel syndrome, and administering to the patient a composition including *Bacillus coagulans* bacteria in dose that reduces one or more symptoms of IBS.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION

Medical diagnosis of IBS was based on the absence or presence of a number of symptoms, which are generally regarded as typical of IBS and are provided, for example, by the "Rome Criteria" (See, W. G. Thompson et al., Gastroent. Int. 2 (1989) 92-95; W. G. Thompson et al., Gut 45/II (1999) II43-II 47; W. G. Thompson, Lancet 341 (1993) 1569-1572), and the Rome II Criteria. Guidelines for IBS diagnosis under the Rome criteria include the continuous or recurrent symptoms of abdominal pain or discomfort that may be relieved with defecation, may be associated with a change in frequency, or may be associated with a change in the consistency of stools; and that two or more of the following symptoms are present at least 25 percent of the time: altered stool frequency (greater than 3 bowel movement per day or less than 3 bowel movements per week), altered stool form (hard or loose watery stools or poorly formed stools), passage of mucous stools, and bloating (feeling of abdominal distention).

The Rome II Diagnostic Criteria (a system for diagnosing functional gastrointestinal disorders based on symptoms) for IBS is as follows:
At least 12 weeks or more, which need not be consecutive, in the preceding 12 months of abdominal discomfort or pain that is accompanied by at least two of the following features:
1) It is relieved with defecation, and/or
2) Onset is associated with a change in frequency of stool, and/or
3) Onset is associated with a change in form (appearance) of stool.

Other symptoms that are not essential but support the diagnosis of IBS:
Abnormal stool frequency (greater than 3 bowel movements/day or less than 3 bowel movements/week); Abnormal stool form (lumpy/hard or loose/watery stool); Abnormal stool passage (straining, urgency, or feeling of incomplete evacuation); Passage of mucus; Bloating or feeling of abdominal distension.

The importance of carbohydrates in the onset of IBS symptoms has recently been discussed. (See, *Scand J. Gastroenterol.* 1998. 33(11):1158-63, *Isr Med Assoc J.* 2000. 2(8):583-7, *Am J. Gastroenterol.* 2003. 98(6):1348-53). IBS and carbohydrate malabsorption have often been confused for one another. Reliable diagnosis is critical to determining the appropriate dosage for treating the symptoms of IBS. The present invention provides diagnostic methods for the detection and diagnosis of IBS in patients, such as humans, who are suffering from IBS, or are at risk of developing IBS.

The present invention also provides methods for the reduction of symptoms of IBS. Prior to the present invention, it has been difficult to effectively reduce symptoms in the treatment of irritable bowel syndrome. The goals of therapeutic treatment were to reduce the variety of complaints, and to improve conditions so as to decrease morbidity and increase the quality of the patient's daily life. Therapeutic treatments include psychotherapy, life guidance, diet therapy, and drug therapy used on a symptomatic basis against the patient's complaints. Compounds including opioid agonists (e.g., loperamide) or anticholinergic agents (e.g., mepenzolate bromide and timepidium bromide) have been used to control hypermotility of the digestive tract, and benzodiazepine drugs (e.g., diazepam) have been prescribed for anxiety, insomnia and similar complaints. Recently, antagonists of 5-hydroxytryptamine (5-HT; serotonin) and 5-HT receptors have been used to treat IBS. (See, U.S. Pat. No. 6,429,209). A deficiency of these treatments is that they are usually incapable of reducing or eliminating multiple symptoms of IBS, particularly when the patient presents with alternations of diarrhea and constipation. The compositions of the present invention alleviate multiple symptoms of carbohydrate malabsorption, including pain, flatus, abdominal bloating, diarrhea, constipation, and alternating diarrhea and constipation The present invention also provides methods of treatment of diseases associated with carbohydrate malabsorption. These diseases, in addition to IBS, include lactose intolerance, fructose intolerance, glucose-galactose intolerance, sorbitol intolerance, short bowel syndrome, stagnant loop syndrome, celiac disease, chronic malnutrition, chronic persistent diarrhea, immunoproliferative small intestinal disease, intractable diarrhea of infancy, postenteritis syndrome, tropical sprue, Whipple's disease, Wolman disease, Crohn's disease and ulcerative colitis.

Bacillus coagulans

Bacillus coagulans is a strain of bacteria that possesses the ability to sporulate, making the strain resistant to heat and other conditions, as well as providing for a long shelf-life in product formulations. Further, Bacillus coagulans is ideal for survival and colonization of tissues under conditions of pH, salinity, and the like within the gastrointestinal tract. Additionally, Bacillus coagulans is non-pathogenic. Preferred methods disclosed herein utilize Bacillus coagulans cells and spores. Methods of preparing Bacillus coagulans vegetative cells and spores are presented in Example 1.

Bacillus coagulans bacteria colonize the gastrointestinal tract of a mammal to which they are provided enterically. Generally, colonization occurs within twenty four to forty eight hours following administration. Efficiency of intestinal colonization of a mammal is determined, e.g., by quantitating the number of Bacillus coagulans bacteria per gram of the mammal's feces. A mammal has been colonized by the Bacillus coagulans bacteria of the present invention if the mammal's feces contain greater than $1\times10^4$ viable bacteria per gram of feces, preferably $1\times10^5$ viable bacteria per gram of feces. Preferably, the feces contain $1\times10^6$ viable bacteria per gram of feces.

One species of Bacillus coagulans, that is useful in this invention, had previously been mischaracterized as a Lactobacillus; this bacterium was labeled as Lactobacillus sporogenes. However, initial classification was incorrect due to the fact that Bacillus coagulans produces spores and through metabolism excretes L(+)-lactic acid, both aspects which provide key features to its utility. Instead, these developmental and metabolic aspects required that the bacterium be classified as a lactic acid Bacillus, and therefore it was re-designated. Accordingly, the bacteria useful in the invention (i) possess the ability to produce and excrete enzymes useful in digestion (e.g., lactase, various proteases, lipases and amylases); (ii) demonstrate beneficial function within the gastrointestinal tract; and (iii) are non-pathogenic.

The Gram positive rods of Bacillus coagulans have a cell diameter of greater than 1.0 μm with variable swelling of the sporangium, without parasporal crystal production. Bacillus coagulans is a non-pathogenic, Gram positive, spore-forming bacteria that produces L(+) lactic acid (dextrorotatory) under homo-fermentation conditions. It has been isolated from natural sources, such as heat-treated soil samples inoculated into nutrient medium (see e.g., Bergey's Manual of Systemic Bacteriology, Vol. 2, Sneath, P. H. A. et al., eds., Williams & Wilkins, Baltimore, Md., 1986). Purified Bacillus coagulans strains have served as a source of enzymes including endonucleases (e.g., U.S. Pat. No. 5,200,336); amylase (U.S. Pat. No. 4,980,180); lactase (U.S. Pat. No. 4,323,651) and cyclomalto-dextrin glucano-transferase (U.S. Pat. No. 5,102,800). In particular, Bacillus coagulans strains have been used as general nutritional supplements and agents to control constipation and diarrhea in humans and animals.

Various Bacillus coagulans bacterial strains which are currently commercially available from the American Type Culture Collection (ATCC, Manassas, Va.) include the following accession numbers: Bacillus coagulans Hammer NRS 727 (ATCC No. 11014); Bacillus coagulans Hammer strain C (ATCC No. 11369); Bacillus coagulans Hammer (ATCC No. 31284); and Bacillus coagulans Hammer NCA 4259 (ATCC No. 15949). Purified Bacillus coagulans bacteria are also available from the Deutsche Sarumlung von Mikroorganismen und Zellkuturen GmbH (Braunschweig, Germany) using the following accession numbers: Bacillus coagulans Hammer 1915 (DSM No. 2356); Bacillus coagulans Hammer 1915 (DSM No. 2383, corresponds to ATCC No. 11014); Bacillus coagulans Hammer (DSM No. 2384, corresponds to ATCC No. 11369); and Bacillus coagulans Hammer (DSM No. 2385, corresponds to ATCC No. 15949). Bacillus coagulans bacteria can also be obtained from commercial suppliers such as K.K. Fermentation (Kyoto, Japan) and Nebraska Cultures (Walnut Creek, Calif.). Compositions include strains or variants derived from Bacillus coagulans Hammer strain ATCC No. 31284 such as ATCC PTA-6085, PTA-6086, or PTA-6087.

Bacillus coagulans bacteria are provided in amounts sufficient to colonize the gastrointestinal tract of a mammal. The invention provides Bacillus coagulans bacteria at a concentration of from about $1\times10^4$ to about $1\times10^{12}$ viable bacteria, specifically about $1\times10^6$ to about $1\times10^{11}$, more specifically about $1\times10^8$ to about $1\times10^{10}$, and most specifically about $810^8$. Bacillus coagulans bacteria are provided as vegetative cells, spores, or a combination thereof.

Fructase

The fructase of the invention is an enzyme that catalyzes the hydrolysis of fructose in the gastrointestinal tract of a mammal. Fructase is purified from a fungus such as Aspergillus oryzae. Fructase is also commercially available from Specialty Enzymes and Biochemicals (Chino, Calif.), Spectrum Chemicals (Los Angeles, Calif.), and Solvay Enzymes (Edison, N.J.).

Fructase activity is measured in vivo using the hydrogen ion breath test. A patient who has abstained from carbohydrates for at least twelve hours is given a 33% fructose solution (50 g per 150 ml of water), and end-expiratory breath samples are collected before (the baseline value) and every 15-30 minutes for four to six hours after sugar ingestion. Hydrogen (and other gases such as methane) breath concentrations are measured using gas chromatography. A person is defined as fructose intolerant if a rise of at least 3 parts per million (ppm) over three consecutive breath tests from the baseline value or a value over 20 ppm following sugar ingestion is observed.

Lactase

The lactase of the invention is an enzyme that catalyzes the hydrolysis of lactose in the stomach and/or intestine. In certain embodiments, two lactases with different optimum pH ranges are used (e.g., a first lactase that has an optimum pH range that encompasses pH 3.0 to about pH 6.0, and a second lactase that preferably has an optimum pH range that encompasses about pH 6.0 to about pH 8.0). An optimum pH range means the pH over which the hydrolytic activity of the lactase is within about 10 to 100 percent of its maximum, and optimum pH value means the pH at which the lactase exhibits maximum hydrolytic activity.

Lactases derived from fungi are generally known to have optimum pH values which fall within the acid range. Genera of fungi useful in obtaining lactases include Aspergillus; Mucor; Fusarium; Scopuloriopsis; Alternaria; and Curvularia and the bacterium Thermus aquaticus. The lactases, having the optimum pH value shown in the parentheses, are preferably derived from the following fungi: Aspergillus oryzae; (4.5-5.0) Aspergillus niger (3.0-4.0); Fusarium moniliforme (3.8-5.0); Scopulariopsis (3.6-5.0); Mucor pucillus (4.5-6), Alternaria alternara (4.5-5.3); and Curvularia inaegualis (3.4-4.3) and the bacterium Thermus aquaticus (4.5-5.5).

Lactases derived from yeast and bacteria are generally known to have optimum pH values in the more neutral region, including Kluyveromyces (Saccharomyces), Lactobacillus,

*Bacillus, Streptococcus,* and *Escherichia.* Lactase derived from the following organisms, having the optimum pH value shown in the parentheses, are preferred: *Kluyveromyces lactis* (6.5), *Kluyveromyces fragilis* (6.6), *Lactobacillus thermophilus* (6.2-7.1), *Bacillus circulans* (6.0), *Lactobacillus bulgaricus* (7.0), *Leuconostoc citrovorum* (56.5), *Bacillus stearothermophilus* (6.0-6.4), *Streptococcus thermophilus* (6.5-7.5), and *Bacillus* sp. (6.8).

The lactases used in the present invention are produced by a variety of well known techniques. Many of these lactases are produced by commercial processes which cultivate the bacterium, yeast or fungus, and then isolate the lactase from the culture or culture broth of the microorganism. Further techniques for preparing such lactases may be found in U.S. Pat. No. 3,629,073; U.S. Pat. No. 3,718,739; and U.S. Pat. No. 3,919,049, all of which are hereby incorporated by reference.

Lactase activity is measured in vivo using the hydrogen ion breath test. A patient who has abstained from carbohydrates for at least twelve hours is given a lactose solution (18-50 g), and end-expiratory breath samples are collected before and every 15-30 minutes for four to six hours after sugar ingestion. Hydrogen (and other gases such as methane) breath concentrations are measured using gas chromatography. An increase in breath hydrogen concentration of 10 parts per million (ppm) following sugar ingestion is typically observed in non-lactose intolerant patients. Incomplete absorption of carbohydrate is defined as an increase in breath hydrogen of 20 ppm (or its equivalent of 5 ppm in methane) following sugar ingestion.

Lactase activity is quantified in units. An FCC lactase unit (FCC Lac U), and IU and a neutral lactase unit are defined as that quantity of enzyme that will liberate 1 μmol of o-nitrophenol from o-nitrophenyl-β-D-galactoside per minute under the conditions, of the assay described in Food Chemicals Codex, National Academy Press, Wash., D.C., pp. 491-2 (1981), which is hereby incorporated by reference, at pH 4.5 and 6.5, respectively.

Other Gastrointestinal Enzymes

Amylase (α-1,4-glucan 4-glucanohydrolase, EC 3.2.1.1.) activity is determined using the method of Somogyi (See, Somogyi, 1960. "Modification of two methods for the assay of amylase." *Clin Chem.* 6:23-35). One amylase activity unit is defined as the amount of amylase that will cause the formation of reducing power equivalent to 1 mg glucose in 30 minutes at 40 degrees C. per milligram of intestinal digesta protein. Cornstarch is an amylase substrate useful for calibration of amylase activity units.

Lipase (e.g., lps aw 02513, triacylglycerol lipase, EC 3.1.1.3.) activity is assayed using the method of Tietz and Fiereck (See, Tietz and Fiereck, 1966. Clin. Chim. Acta 13:352-58). One lipase activity unit is equal to the volume (mL) of 0.05 M NaOH required to neutralize the fatty acid liberated during a 6 hour incubation with 3 mL of lipase substrate (e.g., olive oil) at 37 degrees C. per milligram of digesta protein. Lipases can be purified from *Bacillus subtilis* and *Pseudomonas aruginosa* and are also commercially available.

Peptidases and proteases include enzymes that degrade a polypeptide by hydrolysis of the peptide bonds. Peptidases include amino-, dipeptidyl-, and tripeptidyl-peptidases. Useful proteases include Arg-C proteinase, Asp-N endopeptidase, caspases, chymotrypsin, clostripain, enterokinase, granzyme B, glutamyl endopeptidase, pepsin, proline-endopeptidase, proteinase K, Staphylococcal peptidase I, thermolysin, thrombin and trypsin.

Composition Formulations

The compositions of the present invention are combined with a pharmaceutically acceptable carrier and are preferably administered orally. The unit dosages of these compositions may be in the form of solid preparations, such as tablets, pills, capsules, caplets, powders, granules and wafers, or liquid preparations, such as suspensions or dispersions in aqueous or non-aqueous vehicles, such as syrups and elixirs.

The compositions of the present invention optionally contain components in addition to the *Bacillus coagulans* bacteria. Additional components include supplementary enzymes, anti-diarrheal agents, anti-gas agents, laxatives, dietary fibers, isolated amino acids, vitamins, minerals, antibiotics, and buffering agents.

Supplementary enzymes include a lactase, a fructase, a lipase, and a protease. Generally, a supplementary enzyme is provided in an amount exceeding the amount of the enzyme contained in or produced by the *Bacillus coagulans* bacteria provided in the therapeutic composition. For example, a supplemental lactase is an amount of purified lactase that is administered to digest the lactose present in the gastrointestinal tract of a mammal.

Anti-diarrheal agents include any compounds that reduce diarrhea, such as by reducing water content in the stool. Preferred anti-diarrheal agents include loperamide (such as loperamide HCL), attapulgite, Croton Lechleri Extract, and calcium polycarbophil.

Anti-gas agents include compounds that reduce gas in the gastrointestinal tract of a mammal. Preferred anti-gas agents include α-galactosidase enzyme, simethicone, calcium carbonate, aluminum hydroxide or magnesium hydroxide.

Laxatives include any compound that increases stool density or frequency of bowel movements. Preferred laxatives include senosides, docusate sodium, magnesium hydroxide, and a dietary fiber. Senosides include hydroxyanthracene glycosides such as senosides A, B, C or D, generally obtained from pulverized *Cassia acustifolia* husk. Exemplary dietary fibers include psyllium husk, soy fiber, citrus fiber, beet fiber, pumpkin seed meal, ground flax, black walnut hull, rice fiber, hydrocollodial polysaccharides, pecan husks, and peanut husks.

Isolated amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Preferably, the isolated amino acid is lysine.

The compositions are usable in the form of medicines, foods, and drinks, including supplements, medical foods, health foods, nutraceuticals, and dietary supplements, as directed by a healthcare practicioner. A medical food is prescribed by a physician when a patient has special nutrient needs in order to manage a disease or health condition such as IBS or carbohydrate malabsorption, and the patient is under the physician's ongoing care.

In preparing solid unit dosage forms, the compositions of the present invention (e.g., *Bacillus coagulans* bacteria) are mixed with conventional solid fillers or carriers, such as silicone, starch, talc, calcium phosphate, calcium sulfate, calcium stearate, magnesium stearate, stearic acid, sorbitol, mannitol, gelatin, natural or synthetic gums, such as carboxymethylcellulose, methylcellulose, alginates, dextrans, acacia gum, karaya gum, locust bean gum, tragacanth and other conventional carriers. Additionally, other excipients such as diluents, binders, lubricants, disintegrants, colors and flavoring agents may be employed.

Suitable liquid forms of the present invention can be prepared by incorporating the lactase in aqueous or non-aqueous dispersions, suspensions, or solutions. Conventional liquid carriers such as glycerol, and edible glycols, edible oils, such as cottonseed oil, soybean oil, corn oil, peanut oil, safflower oil, and other triglyceride oils, and dispersing or suspending agents, such as the aforementioned natural and synthetic gums.

Conventional methods are employed for preparing the solid and liquid forms of the present invention. Suitable techniques are described in *Remington's Pharmaceutical Sciences,* 18th Ed., Chapters 83 and 89 (1990), which is hereby incorporated by reference.

The compositions are produced in powdered or granular form for direct admixture with food products consumed by subjects suffering from IBS or other carbohydrate malabsorption diseases. For instance, in the case of a lactose intolerant infant, a suitable amount of the *Bacillus coagulans* and lactase-containing composition, in a powdered or granular form, is added directly to the milk or other food consumed by the infant. In the case of an animal, such as a mammal, that normally requires a dietary regime of whey, the compositions of the present invention may be added directly to the whey.

The composition optionally contains an enteric coating, such as coating of a *Bacillus coagulans* bacterium as a vegetative cell. This coating remains intact in the stomach, but dissolves and release the vegetative cell once it reaches the more neutral environment of the small intestine. Suitable enteric coatings include amylose acetate phthalates, styrene-maleic acid copolymer, cellulose acetate succinate, cellulose acetate phthalate, polyvinyl acetate phthalate, hydroxy-propylmethylcellulose phthalate, fatty acids, fatty acid esters, glycerol esters, polyglycerol esters, paraffin waxes, carnauba wax, formalized gelatin, shellac and hydrogenated vegetable waxes, such as hydrogenated castor oil and cottonseed oil. Other suitable enteric coatings are disclosed in Liebernan, H. A. et al., *Pharmaceutical Dosage Forms: Tablets,* Vol. 3, pp. 114-116 (1990), which is hereby incorporated by reference. The enteric coating is applied using conventional particle coating techniques. If the vegetative cell is granulated with other excipients, the resulting granule may also be coated with the enteric material.

Diagnosis of IBS in Mammals

The guidelines for IBS diagnosis promulgated under the Rome criteria are focused upon subjective symptoms, including the continuous or recurrent symptoms of abdominal pain or discomfort that may be relieved with defecation, a change in frequency or consistency of stools, and that, at least 25 percent of the time, the patient experiences altered stool frequency (greater than 3 bowel movement per day or less than 3 bowel movements per week), altered stool form (hard or loose watery stools or poorly formed stools), passage of mucous stools, or bloating (feeling of abdominal distention). The present invention provides a method of diagnosing irritable bowel syndrome in a patient, based on the patient's malabsorption of carbohydrates. A patient that has one or more IBS symptoms (e.g., a symptom classified under the Rome Criteria) is identified, and a biological sample is obtained from this identified patient. The biological sample can be, e.g., fecal material, urine, blood, serum, plasma, or breath. The amount of a product of a gastrointestinal enzyme in the patient-derived sample is then determined. For example, the hydrogen gas breath test is used to measure hydrogen gas, which is produced as a result of breakdown of unabsorbed carbohydrates in the gastrointestinal tract. The amount of the product in the patient-derived sample is compared with a reference amount of a product of a gastrointestinal enzyme. This reference amount is obtained from a patient or plurality of patients known not to have IBS or other disorders involving carbohydrate malabsorption. An alteration in the test amount relative to the reference amount indicates that the patient has irritable bowel syndrome. For example, an increase in hydrogen gas in a patient-derived sample as compared to a reference sample, measured as described above, indicates poor carbohydrate absorption in the gastrointestinal tract of the patient, leading to the diagnosis of IBS.

Therapeutic Administration

A therapeutic regimen is carried out by identifying a subject, e.g., a human patient suffering from (or at risk of developing) IBS and providing treatment to the subject. For example, patients characterized as producing less than normal amounts of enzymes that degrade carbohydrates, e.g. lactase or fructase, or other digestive enzymes such as amylases, lipases or proteases, are diagnosed as suffering from or at risk of developing IBS, as now described. A composition including *Bacillus coagulans* bacteria is administered to the patient, such as by oral administration, such that one symptom of IBS is reduced. In embodiments of the invention, the patient is a female, such as a post-menstrual female, since symptoms of IBS are often more prevalent and/or severe in post-menstrual women. The patient may be a post-menopausal woman. The composition including *Bacillus coagulans* bacteria is provided prior to or concomitant with the onset of one or more symptoms of IBS.

Prior to the present invention, dietary management of IBS and other diseases associated with carbohydrate malabsorption has focused on the dietary control of a patient's intake of carbohydrate. The invention provides a method of dietary management of a subject's carbohydrate absorption, by identifying a patient having a symptom of carbohydrate malabsorption, and providing *Bacillus coagulans* bacteria to the subject, which then colonize the subject's gastrointestinal tract, and cause the subject's carbohydrate absorption to be modulated. Colonization of *Bacillus coagulans* bacteria in the subject's small and large intestine increases absorption of dietary carbohydrates including fructose and lactose, therefore reducing pain, abdominal bloating, flatus, diarrhea, constipation, and other symptoms of carbohydrate malabsorption.

The methods allow a clinician to tailor carbohydrate malabsorption treatment to more effectively manage patient health and wellness. When a patient presents with one or more symptoms of IBS, the physician is able to determine the extent of the patient's carbohydrate malabsorption by measuring the product of a gastrointestinal enzyme such as fructase or lactase in a sample derived from the patient. Measurement of the enzymatic product is performed by methods known in the art and disclosed herein, including the hydrogen and methane breath tests. The physician then provides the compositions described herein in amounts that reduce or eliminate one or more symptoms of IBS.

A therapeutic system for treating, reducing and/or controlling carbohydrate malabsorption is in the form of a package containing a therapeutic composition containing *B. coagulans* and a supplementary digestive enzyme in combination with packaging material. The packaging material includes a label or instructions for use of the components of the package. The instructions describe the use of the packaged component as described herein for the methods or compositions of the invention.

By way of example, and not of limitation, a system can comprise one or more unit dosages of a composition according to the present invention. Alternatively, the system can alternately contain bulk quantities of a composition. The label contains instructions for using the therapeutic composition in either unit dose or in bulk forms as appropriate, and may also include information regarding storage of the composition, disease indications, dosages, routes and modes of administration and the like information. Furthermore, depending upon the particular contemplated use, the system may optionally contain either combined or in separate packages one or more of the following components: bifidogenic oligosaccharides, flavorings, carriers, and the like components. One particularly preferred embodiment comprises unit dose packages of *Bacillus coagulans* bacteria, for use in combination with a conventional liquid product, together with instructions for combining the bacteria with the liquid product, for use in a therapeutic method.

The methods and compositions described herein are useful in the treatment of Celiac disease. Celiac disease is a hereditary disorder that is caused by sensitivity to the gliadin fraction of gluten, a cereal protein found in wheat and rye and less so in barley and oats. The prevalence of celiac disease varies from about 1:300 in southwest Ireland to about 1:5000 in North America. No single genetic marker exists. Celiac disease may be asymptomatic, but most patients have steatorrhea that can range from mild to massive. Symptoms are usually absent until food containing gluten has been eaten. The subject then begins to pass pale, malodorous, bulky stools, and suffers painful abdominal bloating. Thus, a diagnosis is made on the basis of the symptoms and signs, enhanced by laboratory and x-ray studies, and confirmed by biopsy showing a flat mucosa and by subsequent clinical and histologic improvement on a gluten-free diet. Also, the 5-g D-xylose test is usually abnormal, and untreated patients have low C3 and C4, which rise with gluten withdrawal, and normal or increased serum IgA; in 33% to 50%, IgM is reduced.

EXAMPLES

Example 1

Preparation of *Bacillus coagulans*

I. Preparation of Vegetative *Bacillus coagulans*

*Bacillus coagulans* is aerobic and facultative, and is typically cultured at pH 5.7 to 6.8, in a nutrient broth containing up to 2% (by wt) NaCl, although neither NaCl, nor KCl are required for growth. A pH of about 4.0 to about 7.5 is optimum for initiation of sporulation (i.e., the formation of spores). The bacteria are optimally grown at 20° C. to 45° C., and the spores can withstand pasteurization. Additionally, the bacteria exhibit facultative and heterotrophic growth by utilizing a nitrate or sulfate source. However, *Bacillus coagulans* strains and their growth requirements have been described previously (see e.g., Baker, D. et al, 1960. *Can. J. Microbiol.* 6: 557-563; Nakamura, H. et al, 1988. *Int. J. Syst. Bacteriol.* 38: 63-73. In addition, various strains of *Bacillus coagulans* can also be isolated from natural sources (e.g., heat-treated soil samples) using well-known procedures (see e.g., *Bergey's Manual of Systemic Bacteriology*, Vol. 2, p. 1117, Sneath, P. H. A. et al., eds., Williams & Wilkins, Baltimore, Md., 1986).

*Bacillus coagulans* is cultured in a variety of media, although it has been demonstrated that certain growth conditions are more efficacious at producing a culture which yields a high level of sporulation. For example, sporulation is demonstrated to be enhanced if the culture medium includes 10 mg/l of $MgSO_4$ sulfate, yielding a ratio of spores to vegetative cells of approximately 80:20. In addition, certain culture conditions produce a bacterial spore which contains a spectrum of metabolic enzymes particularly suited for the present invention (i.e., production of lactic acid and enzymes for the enhanced probiotic activity and biodegradation). Although the spores produced by these aforementioned culture conditions are preferred, various other compatible culture conditions which produce viable *Bacillus coagulans* spores may be utilized in the practice of the present invention.

Suitable media for the culture of *Bacillus coagulans* include: TSB (Tryptic Soy Broth), GYE (Glucose Yeast Extract Broth), and NB (nutrient broth), which are all well-known within the field and available from a variety of sources. Media supplements which contain enzymatic digests of poultry and/or fish tissue, and containing food yeast are particularly preferred. A preferred supplement produces a media containing at least 60% protein, and about 20% complex carbohydrates and 6% lipids. Media can be obtained from a variety of commercial sources, notably DIFCO (Newark, N.J.); BBL (Cockeyesville, Md.); and Troy Biologicals (Troy, Md.

II. Preparation of *Bacillus coagulans* Spores

Dried *Bacillus coagulans* Hammer bacteria (ATCC No. 31284) spores—prepared as follows. Approximately $1 \times 10^7$ spores were inoculated into one liter of culture medium containing: 30 g (wt./vol.) Tryptic Soy Broth; 10 g of an enzymatic-digest of poultry and fish tissue; and 10 g $MnSO_4$. The culture was maintained for 72 hours under a high oxygen environment at 37° C. so as to produce a culture having approximately $6 \times 10^9$ cells/gram of culture. The culture was then centrifuged to remove the liquid culture medium and the resulting bacterial paste was re-suspended in 100 ml of sterile water and 20% malto-dextrin and lyophilized. The lyophilized bacteria were ground to a fine powder by use of standard good manufacturing practice (GMP) methodologies.

Example 2

Therapeutic Formulations

Formulation #1
  *Bacillus coagulans* (800 Million CFU)
  Manganese Stereate
  Methyl Cellulose
  Blue LakeDye
Formulation #2
  *Bacillus coagulans* (800 Million CFU)
  Fructose (3,000 units)
  Lactose (3,000 units)
  Lipase (1,500 units)
  Manganese Stereate
  Methyl Cellulose
Formulation #3
  *Bacillus coagulans* (800 Million CFU)
  Dibasic Calcium Phosphate
  Loperamide HCl (2 mg)
  Methyl Cellulose
  Manganese Stereate
  Blue Lake Dye
Formulation #4
  *Bacillus coagulans* (800 Million CFU)
  Senosides
  Dibasic Calcium Phosphate
  Loperamide HCl (2 mg)
  Methyl Cellulose
  Manganese Stereate
  Blue Lake Dye Formulation #5

| Formulation #5 | |
| --- | --- |
| Lactase | 3,000 FCC units |
| Fructase | 2,000 FCC units |
| Micro-Crystalline Cellulose | |
| Manganese Stearate | |
| Blue Lake Dye #1 | |
| Raspberry Flavor | |
| Aspartame | |

Formulation #6

| Lactase | 3,000 FCC units |
| --- | --- |
| Fructase | 2,000 FCC units |
| Psylium Husks | |
| Micro-Crystalline Cellulose | |
| Manganese Stearate | |
| Blue Lake Dye #1 | |

Formulation #7

| Loperamide | 2 mg |
| --- | --- |
| Lactase | 3,000 FCC units |
| Fructase | 2,000 FCC units |
| Micro-Crystalline Cellulose | |
| Manganese Stearate | |
| Blue Lake Dye #1 | |

Formulation #8

| Senosides | |
| --- | --- |
| Lactase | 3,000 FCC units |
| Fructase | 2,000 FCC units |
| Micro-Crystalline Cellulose | |
| Manganese Stearate | |
| Blue Lake Dye #1 | |

Formulation #9

| Lysine | 125 mg |
| --- | --- |
| Bacillus coagulans (1.5 × $10^{10}$ CFU/g) | 53.3 mg |
| Nu Tab | 358 mg |
| Mannitol | 350 mg |
| Red sugar specks | 16 mg |
| Magnesium Stearate | 8 mg |
| Flavor-906.300 (Raspberry) | 4 mg |
| FD&C Blue #1 Lake | 0.2 mg |

Formulation #10
Bacillus coagulans (8.0×$10^8$ CFU)
L-lysine
cellulose
magnesium Stearate
hydroxypropylmethylcellulose
maltodextrin
favor
FD&C blue lake dye
red sucrose specks

OTHER EMBODIMENTS

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims.

What is claimed is:

1. A method of reducing a symptom of irritable bowel syndrome, comprising the steps of: identifying a subject having a symptom of irritable bowel syndrome; and providing a composition comprising an effective amount of viable *Bacillus coagulans* bacterial spores to said subject, wherein said bacterial spores are from *Bacillus coagulans* selected from the group consisting of GBI-20 (ATCC Designation Number PTA-6085), GBI-30 (ATCC Designation Number PTA-6086), and GBI-40 (ATCC Designation Number PTA-6087), wherein said composition comprising *Bacillus coagulans* is administered orally, and wherein a symptom of irritable bowel syndrome in said subject is reduced following said administration.

2. The method of claim 1, wherein said composition further comprises a supplementary enzyme, wherein said enzyme is selected from the group consisting of a lactase, a fructase, a lipase, an amylase and a protease.

3. The method of claim 1, wherein said symptom is gas or bloating.

4. The method of claim 1, wherein said composition further comprises an anti-gas agent.

5. The method of claim 4, wherein said anti-gas agent is selected from the group of α-galactosidase enzyme, simethicone, calcium carbonate, aluminum hydroxide and magnesium hydroxide.

6. The method of claim 1, wherein said composition comprises about 1×$10^8$ to about 1×$10^{10}$ *Bacillus coagulans* bacterial spores.

7. A method of reducing a symptom of irritable bowel syndrome (IBS), comprising identifying a subject suffering from irritable bowel syndrome, and orally administering to said subject a composition comprising an effective IBS-inhibiting amount of *Bacillus coagulans* bacterial spores prior to or concomitant with the onset of one or more IBS symptoms, wherein said bacterial spores are from *Bacillus coagulans* selected from the group consisting of GBI-20 (ATCC Designation Number PTA-6085), GBI-30 (ATCC Designation Number PTA-6086), and GBI-40 (ATCC Designation Number PTA-6087), wherein said composition comprising *Bacillus coagulans* is administered orally, and wherein a symptom of irritable bowel syndrome in said subject is reduced following said administration.

8. The method of claim 7, wherein said composition further comprises a supplementary enzyme, wherein said enzyme is selected from the group consisting of a lactase, a fructase, a lipase, an amylase, and a protease.

9. The method of claim 7, wherein said composition comprises about 1×$10^8$ to about 1×$10^{10}$ *Bacillus coagulans* spores.

10. The method of claim 1, wherein the subject is a human.

11. The method of claim 7, wherein the subject is a human.

12. The method of claim 1, wherein said *Bacillus coagulans* is GBI-30 strain (ATCC Designation Number PTA-6086).

13. The method of claim 7, wherein said *Bacillus coagulans* is GBI-30 strain (ATCC Designation Number PTA-6086).

14. A method of claim 1, wherein said composition comprises a ratio of *Bacillus coagulans* bacterial spores to vegetative cells of approximately 80:20.

15. The method of claim 7, wherein said composition comprises a ratio of *Bacillus coagulans* bacterial spores to vegetative cells of approximately 80:20.

16. The method of claim 1, wherein said composition comprises about $1\times10^4$ to about $1\times10^{12}$ *Bacillus coagulans* bacterial spores.

17. The method of claim 7, wherein said composition comprises about $1\times10^4$ to about $1\times10^{12}$ *Bacillus coagulans* bacterial spores.

18. The method of claim 1, wherein said composition comprises about $1\times10^6$ to about $1\times10^{11}$ *Bacillus coagulans* bacterial spores.

19. The method of claim 1, wherein said composition comprises about $8.0\times10^8$ *Bacillus coagulans* bacterial spores.

20. The method of claim 7, wherein said composition comprises about $1\times10^6$ to about $1\times10^{11}$ *Bacillus coagulans* bacterial spores.

21. The method of claim 7, wherein said composition comprises about $8.0\times10^8$ *Bacillus coagulans* bacterial spores.

\* \* \* \* \*